(12) United States Patent
Intoccia, Jr. et al.

(10) Patent No.: US 10,327,881 B2
(45) Date of Patent: Jun. 25, 2019

(54) IMPLANTABLE MEDICAL DEVICE AND METHODS OF DELIVERING AN IMPLANTABLE MEDICAL DEVICE

(71) Applicant: Boston Scientific Scimed, Inc., Maple Grove, MN (US)

(72) Inventors: Alfred P. Intoccia, Jr., Nashua, NH (US); Ronald Ciulla, Westford, MA (US); Kenneth Daignault, Holden, MA (US); Michael F. Weiser, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 842 days.

(21) Appl. No.: 14/204,947

(22) Filed: Mar. 11, 2014

(65) Prior Publication Data

US 2014/0275745 A1    Sep. 18, 2014

Related U.S. Application Data

(60) Provisional application No. 61/777,209, filed on Mar. 12, 2013.

(51) Int. Cl.
*A61F 2/00* (2006.01)

(52) U.S. Cl.
CPC ................. *A61F 2/0036* (2013.01)

(58) Field of Classification Search
CPC .... A61F 2/0054; A61F 2/0031; A61F 2/0004; A61F 2/0009
USPC ........................................................ 600/31
See application file for complete search history.

(56) References Cited

U.S. PATENT DOCUMENTS

| | | | |
|---|---|---|---|
| 3,903,894 A | | 9/1975 | Rosen et al. |
| 3,926,184 A | * | 12/1975 | Gehl ............... A61F 2/0054 600/41 |
| 4,549,530 A | | 10/1985 | Finney |
| 4,742,833 A | | 5/1988 | Barsom |
| 5,012,822 A | | 5/1991 | Schwarz |
| 5,184,629 A | * | 2/1993 | Erickson ........... A61F 2/0054 128/885 |
| 6,463,932 B1 | | 10/2002 | Single et al. |
| 6,609,522 B2 | * | 8/2003 | Cheng ............... A61F 2/0054 128/885 |
| 6,659,936 B1 | | 12/2003 | Furness et al. |
| 6,953,429 B2 | | 10/2005 | Forsell |
| 6,981,505 B2 | | 1/2006 | Krause et al. |
| 7,223,228 B2 | | 5/2007 | Timm et al. |
| 7,499,753 B2 | | 3/2009 | Forsell |
| 7,621,863 B2 | | 11/2009 | Forsell |
| 7,648,455 B2 | | 1/2010 | Forsell |
| 7,727,140 B2 | | 6/2010 | Selkowitz |
| 8,753,363 B2 | * | 6/2014 | Anderson ........... A61F 2/0036 600/30 |

(Continued)

*Primary Examiner* — Thaddeus B Cox
(74) *Attorney, Agent, or Firm* — Brake Hughes Bellermann LLP

(57) ABSTRACT

In some implementations, a medical device includes a clamp component and a strap. The clamp component has a portion configured to be placed around a urethra of a patient. The clamp component includes a first end portion configured to be lockably coupled to a second end portion of the clamp component. The strap has a portion extending between a first portion of the portion of the clamp component and a second portion of the portion of the clamp component.

10 Claims, 9 Drawing Sheets

(56) References Cited

U.S. PATENT DOCUMENTS

| | | |
|---|---|---|
| 2002/0153013 A1 | 10/2002 | Single et al. |
| 2004/0143343 A1 | 7/2004 | Grocela |
| 2004/0242956 A1 | 12/2004 | Scorvo |
| 2006/0081265 A1 | 4/2006 | Warden |
| 2006/0161041 A1 | 7/2006 | Forsell |
| 2006/0247490 A1 | 11/2006 | Merade et al. |
| 2006/0276764 A1 | 12/2006 | Warne |
| 2008/0146868 A1 | 6/2008 | Robert et al. |
| 2009/0259093 A1 | 10/2009 | Bhat et al. |
| 2010/0256757 A1 | 10/2010 | Lima et al. |

\* cited by examiner

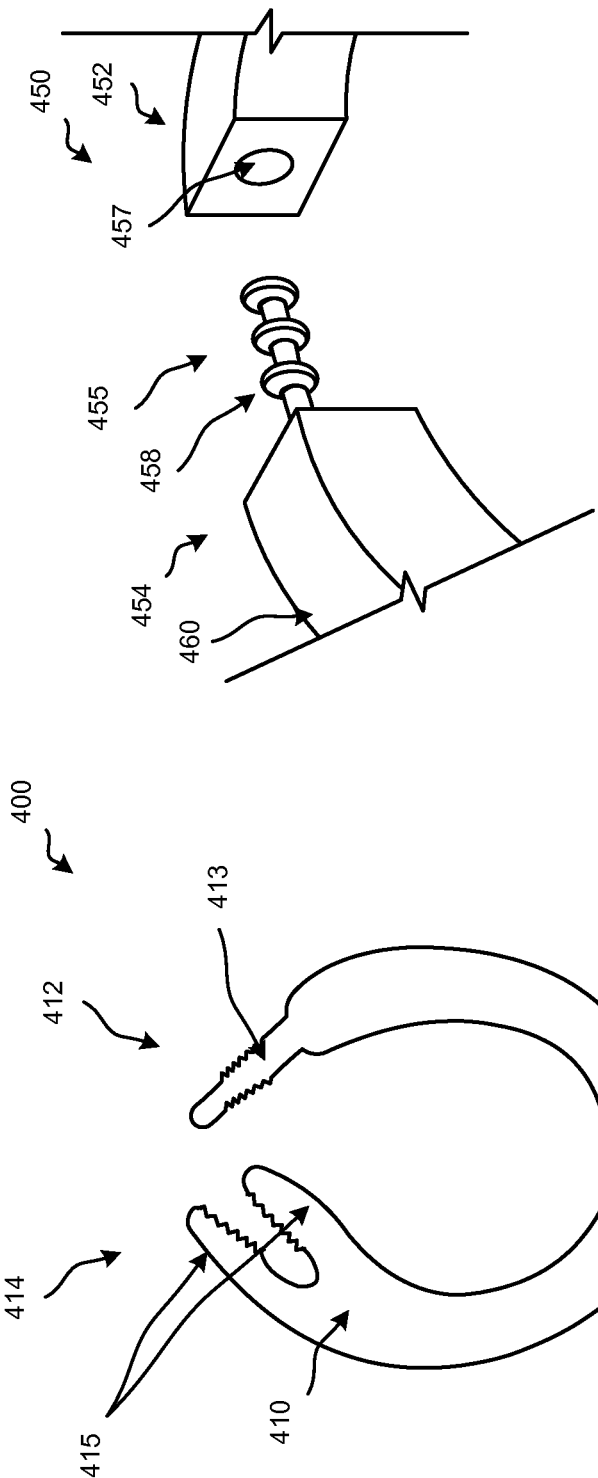

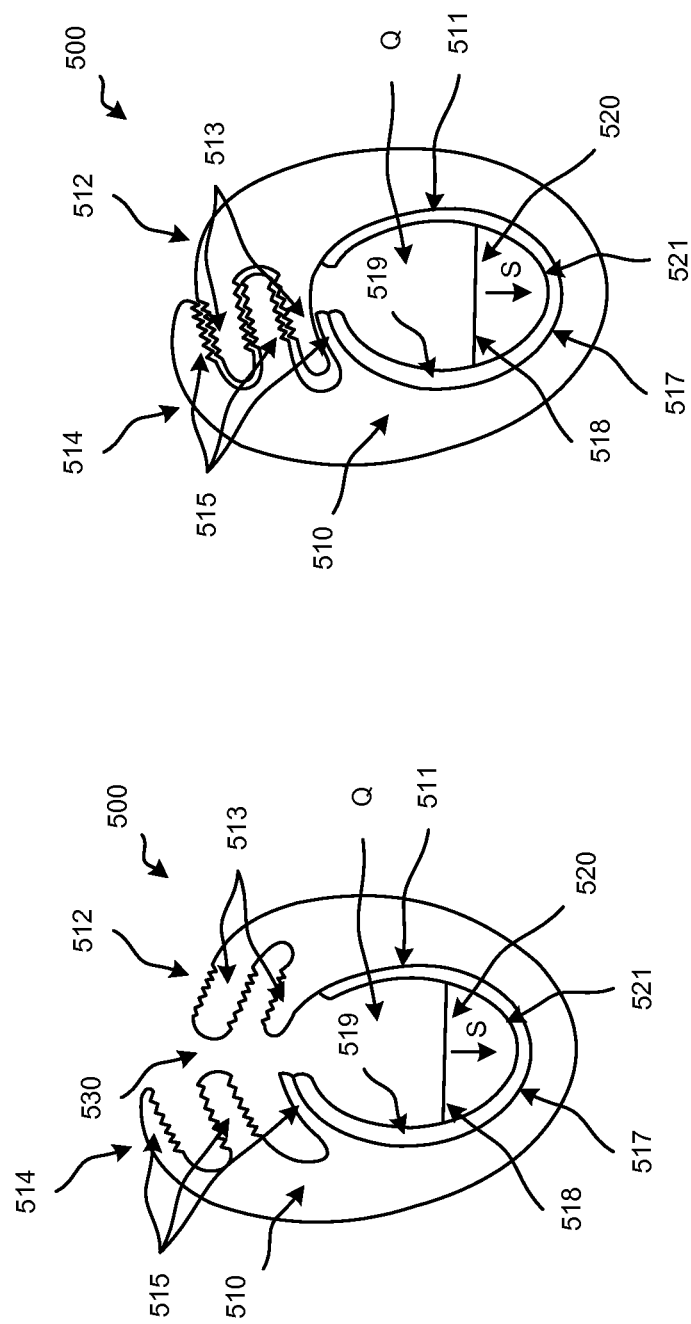

IMPLANTABLE MEDICAL DEVICE AND METHODS OF DELIVERING AN IMPLANTABLE MEDICAL DEVICE

CROSS-REFERENCE TO RELATED APPLICATION

The application is a Nonprovisional of, and claims priority to, U.S. Patent Application No. 61/777,209, filed on Mar. 12, 2013, entitled "IMPLANTABLE MEDICAL DEVICE AND METHODS OF DELIVERING AN IMPLANTABLE MEDICAL DEVICE", which is incorporated by reference herein in its entirety.

TECHNICAL FIELD

The implementations herein generally relate to medical devices and procedures, and, in particular, to devices configured to be delivered and placed into a patient's body for treatment of urinary incontinence.

BACKGROUND

Various types of urinary incontinence, which is the involuntary leakage of urine, can cause a degraded quality of life of a patient. Urinary incontinence, such as stress urinary incontinence (SUI), overflow incontinence, etc., can be caused by a variety of conditions including insufficient strength of the pelvic floor muscles, polyuria (excessive urine production), enlarged prostate in men, and so forth. For example, a relatively large percentage of men who have had a radical prostatectomy or who have had a transurethral resection of the prostate (TURP) may experience stress urinary incontinence. As another example, in some patients, disorders that interfere with the nerve function of the bladder can also lead to incontinence.

A variety of known devices have been developed to treat urinary incontinence. Some of these known devices have been designed to mimic at least some functions of a biological urinary sphincter by constricting a urethra of a patient during urinary storage and permitting the urethra to open during voiding. For example, artificial urinary sphincters with inflatable components used to constrict the urethra have been developed. While effective for some patients, some of these known devices can be expensive to produce and/or maintain, difficult to implant and/or operate after being implanted, difficult to calibrate, can have many moving parts that can independently fail, and so forth.

Thus, there is a need for an improved medical device for urinary incontinence treatment.

SUMMARY

In some implementations, a medical device includes a clamp component and a strap. The clamp component has a portion configured to be placed around a urethra of a patient. The clamp component includes a first end portion configured to be lockably coupled to a second end portion of the clamp component. The strap has a portion extending between a first portion of the portion of the clamp component and a second portion of the portion of the clamp component.

In some implementations, a medical device includes a clamp component and a crimp component. The clamp component has a portion configured to be placed around a urethra of a patient. The clamp component including a first end portion configured to be lockably coupled to a second end portion of the clamp component. The clamp component includes a liner coupled to an inner surface of the portion of the clamp component. The crimp component has a surface extending between a first portion of the portion of the clamp component and a second portion of the portion of the clamp component. The crimp component is a non-inflatable component. In some implementations, the portion of the clamp component is curved or includes a curved portion.

In some implementations, a method includes moving a clamp component having a portion around a urethra of a patient; lockably coupling, after the moving of the clamp component, a first end portion of the clamp component to a second end portion of the clamp component; and adjusting a tension of a strap having a portion extending between a first inner portion of the portion of the clamp component and a second inner portion of the portion of the clamp component.

BRIEF DESCRIPTION OF THE FIGURES

FIGS. 4A and 4B illustrate different locking mechanisms of a medical device.

FIG. 5A illustrates another medical device in an open configuration

FIG. 5B illustrates the medical device shown in FIG. 5A in a closed configuration.

DETAILED DESCRIPTION

In general, the implementations disclosed herein are directed to systems, methods, and devices for treating urinary incontinence. However, the systems, methods and devices may be employed for other treatment purposes related to the flow of a fluid in a lumen of a body of a patient. The term patient may be used hereafter for a person who benefits from the medical device or the methods disclosed in the presented implementations. For example, the patient may be a person whose body receives the medical device disclosed by the present implementations in a surgical treatment. For example, in some implementations, the patient may be a human female, a human male, or any other mammal.

Figure 1A:
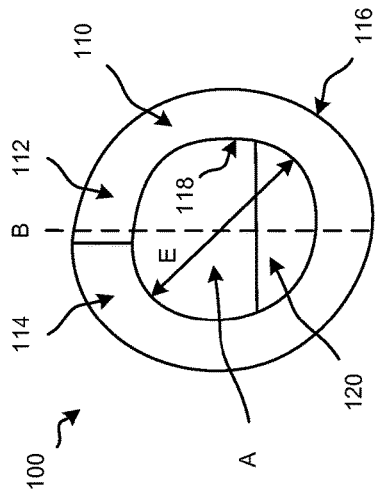
FIGS. 1A and 1B are diagrams that illustrate a medical device configured to be implanted within a body of a patient.
Figure 1B:
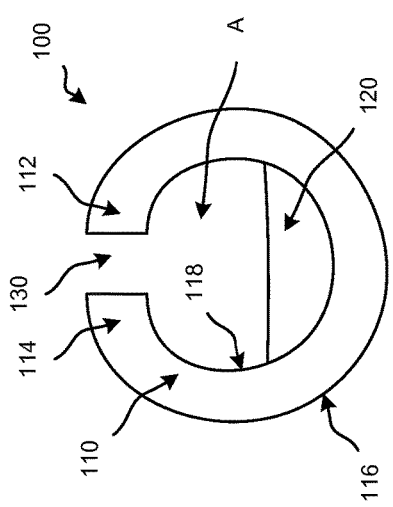
Figure 1C:
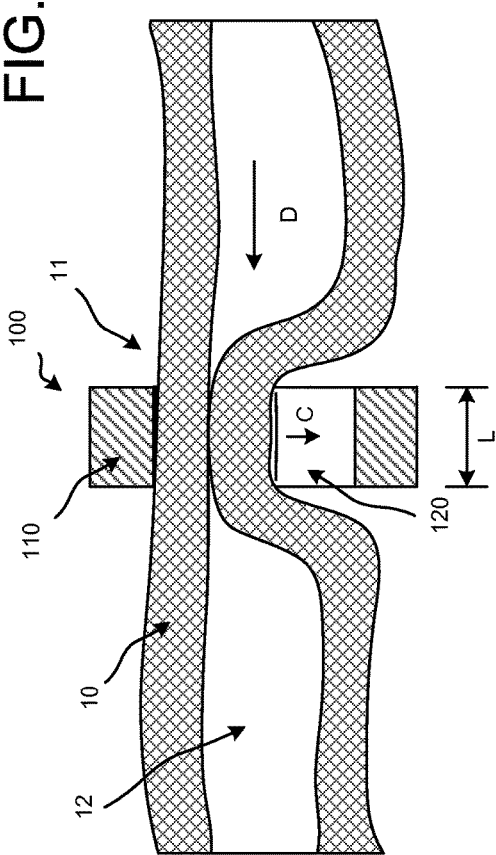
FIG. 1C is a schematic diagram that illustrates a side cross-sectional view of the medical device shown in FIGS. 1A and 1B.

FIGS. 1A through 1C are diagrams that illustrate a medical device 100 configured to be implanted within a body of a patient. In some implementations, the medical device 100 is a bodily implant configured to be coupled to a urethra for the treatment of urinary incontinence. For example, the medical device 100 can be used, during a medical procedure, to treat various dysfunctions, including procedures to treat urinary incontinence. FIG. 1A illustrates the medical device 100 in an open configuration, and FIG. 1B illustrates the medical device 100 in a closed configuration. FIG. 1C illustrates a cross-sectional view of the medical device 100 shown in FIG. 1B when disposed around a urethra 10 of a patient. The cross-sectional view of the medical device 100 shown in FIG. 1C is cut along line B shown in FIG. 1B.

As shown in FIG. 1A, the medical device 100 includes a clamp component 110 and a crimp component 120. The crimp component 120 is coupled to at least a portion of the clamp component 110. When the medical device 100 is in the open configuration shown in FIG. 1A, a gap 130 is disposed between end portions 112, 114 of the clamp component 110. In other words, the end portion 112 may not be in contact with, or maybe separated from, the end portion 114 when in the open configuration. The clamp component 110 is configured to be moved around a urethra 10 (shown in FIG. 1C) of a patient through the gap 130 between the end portions 112, 114 of the clamp component 110. In some implementations, the clamp component 110 can be configured to be flexed so that the size (e.g., length) of the gap 130 can be changed (e.g., increased, decreased) by moving the end portion 112 away from the end portion 114 when the clamp component 110 is moved around the urethra 10 of the patient. In some implementations, the medical device 100 can operate as an artificial urinary sphincter and can be referred to as an artificial urinary sphincter. In some implementations, the clamp component 110 can be configured to function as a collar around the urethra 10.

The clamp component 110 can be moved so that the end portion 112 is coupled to (e.g., lockably coupled to) the end portion 114 when the medical device 100 is in the closed configuration as shown in FIG. 1B. In some implementations, the clamp component 110 can be moved so that the end portion 112 can be decoupled from (e.g., unlocked from) the end portion 114 (after being lockably coupled to the end portion 114). In such implementations, at least a portion of the end portion 112 is in contact with at least a portion of the end portion 114 when in the closed configuration.

When in the open configuration shown in FIG. 1A, the medical device 100 can be moved around the urethra 10 through the gap 130 so that the urethra 10 is disposed within region A defined by the clamp component 110. After the clamp component 110 of the medical device 100 is moved around the urethra 10 through the gap 130, the clamp component 110 of medical device 100 can be changed to the closed configuration shown in FIG. 1B so that the medical device 100 is clamped around (e.g., surrounds) urethra 10. The crimp component 120 is configured to constrict (e.g., kink, lift, at least partially close off) the urethra 10 when the medical device 100 is in the closed configuration around the urethra 10. The cross-sectional view of medical device 100 shown in FIG. 1C illustrates constriction of a portion 11 of the urethra 10 when the medical device 100 is in the closed configuration around the urethra 10.

In some implementations, the medical device 100 can be biased to the closed configuration shown in FIG. 1B. In such implementations, the force can be applied to medical device 100 to move the medical device 100 to the open configuration shown in FIG. 1A.

The medical device 100 is configured to constrict the urethra 10 so that a fluid e.g., urine) is prevented, or substantially prevented, from flowing within the urethra 10 (from a bladder of the patient). The urethra 10 can be constricted so that undesirable leakage associated with urinary incontinence can be prevented or substantially prevented. Medical device 100 can be configured so that voiding can be achieved when a patient bears down. When bearing down, muscles (e.g., bladder muscles, abdominal muscles) are contracted to apply a force that can cause urine to exit the bladder and flow into the urethra 10. Portions of the medical device 100, such as crimp component 120, can be made of a relatively flexible material so that voiding can be achieved through the portion 11 of the urethra 10 when a patient bears down. Specifically, pressure applied to the portion 11 of the urethra 10 by a fluid (along at least direction D, for example) within the urethra can cause the crimp component 120 to flex along at least direction C shown in FIG. 1C so that portion 11 of the urethra 10 may become less constricted (or have a larger opening) and permit flow of a fluid through the urethra 10 (along direction D). In some implementations, the crimp component 120 and/or the clamp component 110 can be made of a material that substantially prevents or does not cause tissue erosion.

In some implementations, the width L can be between a few millimeters and a few centimeters. In some implementations, the width L can be less than a few millimeters or greater than a few centimeters. In some implementations, the width L can vary, taper, etc. around the circumference of the clamp component 110.

Figure 2:
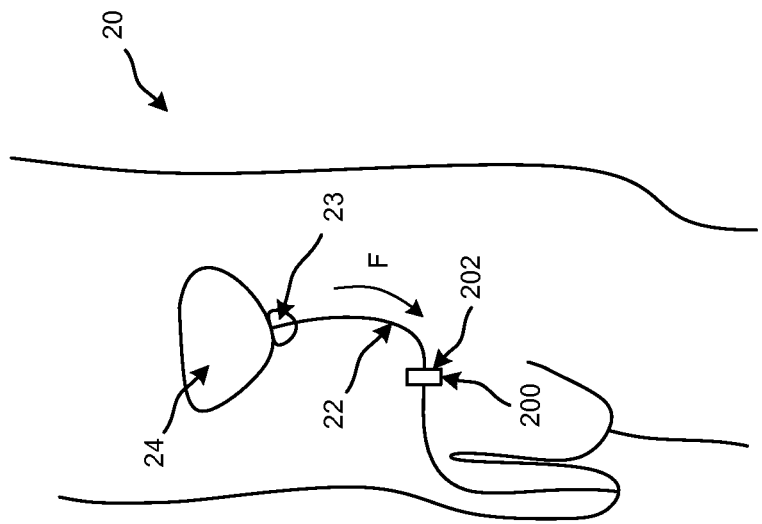
FIG. 2 is a diagram that illustrates placement of a medical device within a body of a patient.

FIG. 2 is a diagram that illustrates placement of the medical device 200 within a body 20 of a male patient. As shown in FIG. 2, the medical device 200 is coupled around the urethra 22 of the patient below a bladder 24 and a prostate 23 of the patient. The medical device 200 is configured to substantially prevent the flow of urine from the bladder 24 through the urethra 22 along direction F until the patient bears down during voiding to push or force urine through the medical device 200. A portion of the medical device 200 can be configured to move (e.g., flex, bend) in response to pressure applied on a bladder side 202 of the medical device 200 by the patient by urine in the urethra 22 so that the urine may exit the body 20 of the patient through the urethra 22. Although FIG. 2 is a diagram that illustrates a male patient, the medical device 200 can similarly be used in a body of a female patient. Also, the medical device 200 can be used for other types of lumens within a body of the patient.

Referring back to FIGS. 1A and 1B, the clamp component 110 defines a curved profile such as a circular profile, or substantially circular profile. Specifically, in this implementation, an inner profile of an inner surface 118 of the clamp component 100 defines a circle and an outer profile of an outer surface 116 the clamp component 110 also defines a circle. In some implementations, the clamp component 110 can have a variety of shapes. For example, in some implementations, an outer surface of the clamp component 110 can define shapes such as square, an oval, a triangle, and/or so forth. An inner surface of the clamp component 110 can define shapes such as square, an oval, a triangle, and/or so forth. In some implementations, an outer surface and or an inner surface of the clamp component 110 can have any combination of flat surfaces and curved surfaces.

In some implementations, the clamp component 110 can be made of a relatively flexible material so that the clamp component 110 can be changed from the open configuration shown in FIG. 1A to the closed configuration shown in FIG. 1B. Although not shown in FIGS. 1A through 1C, in some implementations, the clamp component 110 can have, for example, a hinge, a flexible spring, and/or so forth that enables the clamp component 110 to flex between the open configuration and the closed configuration.

In some implementations, the clamp component 110 can be made of any combination of a plastic material (e.g., a flexible plastic material), a silicone-based material, a rubber material (e.g., a rubber based material) and/or so forth. In some implementations, the clamp component 110 can be made of a single material or multiple materials that can be coupled (e.g., fused) together.

In some implementations, the end portions 112, 114 of the clamp component 110 can be configured so that the end portion 112 can be lockably coupled to the end portion 114 in a variety of positions when the clamp component 110 is in the closed configuration. In other words, the end portions 112, 114 can be adjustably coupled to one another or decoupled from one another. The end portions 112, 114 can be adjustably coupled to one another using a locking mechanism that can include, for example, a latch, a screw, a ratchet mechanism, sliding components, one or more hinges, detents, and/or so forth. In some implementations, the end portion 112 can have at least a portion that is disposed on top of, to the side of, or below the end portion 114 when the end portions 112, 114 are coupled together.

For example, the end portion 112 can be lockably coupled in a first position with respect to the end portion 114 so that the clamp component 110 defines an opening in region A having a first area or volume. The end portion 112 can be moved with respect to the end portion 114 and lockably coupled in a second position with respect to the end portion 114 so that the clamp component 110 defines an opening in region A having a second area or volume different from the first area or volume. In some implementations, the end portions 112, 114 can be removably coupled so that the end portions 112, 114 can be moved from one lockably coupled configuration to another lockably coupled configuration (or even decoupled). More details related to locking mechanisms are described below.

In some implementations, the crimp component 120 can be, or can include, a strip of material. In some implementations, the strip of material can be, for example, a mesh strip, a string, and/or so forth. In some implementations, the strip of material can be suspended across the clamp component 110. In some implementations, the crimp component 120 can be, or can include, a solid component. More details related to crimp components and clamp components are described in connection with the figures below.

Figure 3B:
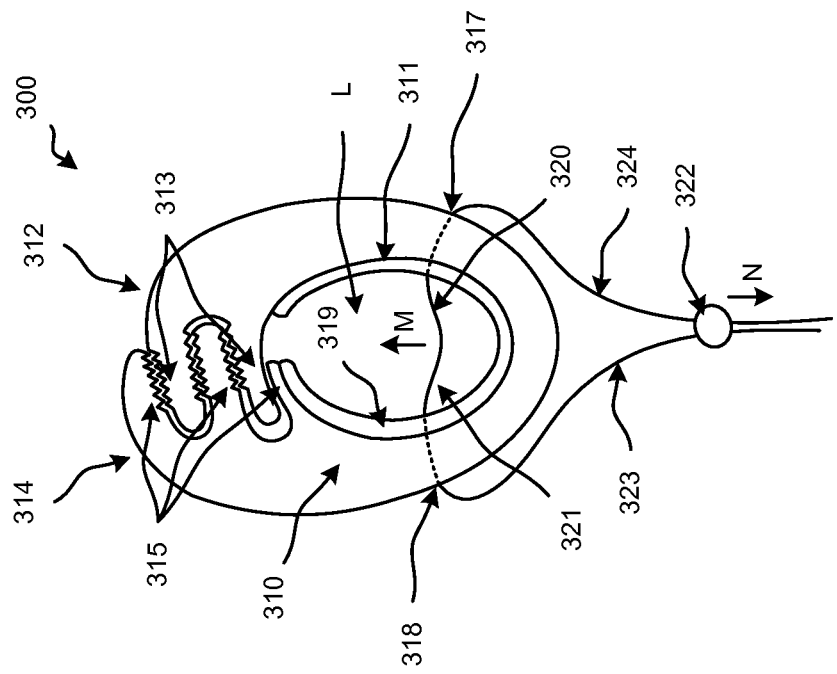
FIGS. 3B and 3C illustrate the medical device shown in FIG. 3A in a closed configuration.
Figure 3A:
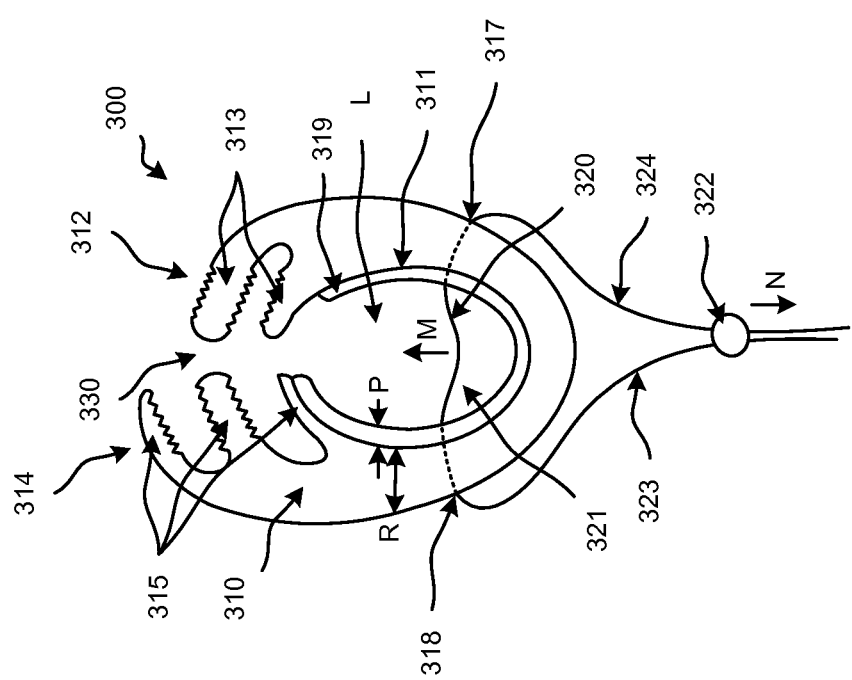
FIG. 3A illustrates a medical device in an open configuration.

FIGS. 3A and 3B are diagrams that illustrate a medical device 300 configured to be implanted within a body of a patient. The medical device 300, which is an implementation of the medical device 100 shown in FIG. 1, is a bodily implant configured to be coupled to, for example, a urethra (not shown) for the treatment of urinary incontinence. The medical device 300 can be used, during a medical procedure, to treat various dysfunctions, including procedures to treat urinary incontinence. FIG. 3A illustrates the medical device 300 in an open configuration, and FIG. 3B illustrates the medical device 300 in a closed configuration.

The medical device 300 shown in FIGS. 3A and 3B can be configured to constrict, for example, a lumen of a patient so that a fluid is prevented, or substantially prevented, from flowing within the lumen. For example, a urethra of a patient can be constricted by the medical device 300 so that undesirable leakage associated with urinary incontinence can be prevented or substantially prevented. The medical device 300 can be configured so that voiding can be achieved when a patient bears down.

As shown in FIG. 3A, the medical device 300 includes a clamp component 310 and a crimp component 320. When the medical device 300 is in the open configuration shown in FIG. 3A, a gap 330 is disposed between end portions 312, 314 of the clamp component 310. In other words, the end portion 312 may not be in contact with, or may be separated from, the end portion 314. The clamp component 310 is configured to be moved around a urethra (not shown) of a patient through the gap 330 between the end portions 312, 314 of the clamp component 310. In some implementations, the clamp component 310 can be configured to be flexed so that the size (e.g., length) of the gap 330 can be changed (e.g., increased, decreased) by moving the end portion 312 away from the end portion 314 when the clamp component 310 is moved around the urethra 30 of the patient.

As shown in FIG. 3A, the end portion 312 includes protrusions 313 and the end portion 314 includes protrusions 315. As shown in FIG. 3B, when the medical device 300 is in the closed configuration, the protrusions 313 of the end portion 312 can be lockably coupled to (e.g., interleaved with) the protrusions 315 of the end portion 314. The protrusions 313 of the end portion 312 can be inserted between the protrusions 315 of the end portion 314. Specifically, teeth of edges of the protrusions 313 can be lockably coupled to teeth of edges of the protrusions 315 when the medical device 300 is in the closed configuration. As shown in FIG. 3B, when the medical device 300 is in the closed configuration, at least a portion of the end portion 312 is in contact with at least a portion of the end portion 314. In this implementation, the end portion 312 includes three protrusions 313 and the end portion 314 includes two protrusions 315. In some implementations, the protrusions can be referred to as fingers, as protruding members, or as lockable members.

In some implementations, the medical device 300 can be configured with different protrusions than those shown in FIGS. 3A and 3B. For example, the end portion 314 can include two protrusions configured to be lockably coupled to a single protrusion of the end portion 312. The end portions 312, 314 can be configured with various types of locking mechanisms. In some implementations, the end portions 312, 314 can collectively be referred to as, or can define, a locking mechanism. In some implementations, the locking mechanism can include a latch, a screw, a ratchet mechanism, sliding components, one or more hinges, detents, Velcro, magnets and/or so forth. Examples of different locking mechanisms are shown in FIGS. 4A and 4B. It is should be understood that the interlocking protrusion components may comprise any size, shape and orientation feasible to achieve a mechanical lock between the two end portions 312 and 314. In some implementations the interlock or coupling is aided by protrusions in any of 3 dimensions (e.g., protrusions may have smaller protrusions in any of 3 dimensions.

As shown in FIG. 4A, a clamp component 410 of the medical device 400 includes protrusions 415 of an end portion 414 configured to be lockably coupled to a single protrusion 413 of an end portion 412. The medical device 400 includes less protrusions overall than the medical device 300 shown in FIGS. 3A and 3B.

FIG. 4B is a diagram that illustrates another example of a locking mechanism 450, according to an implementation. As shown in FIG. 4B the locking mechanism 450, includes teeth 458 on a protrusion 455 of an end portion 454 of a clamp component 460 of a medical device that can be inserted into an opening 457 of an end portion 452 of the clamp component 460 of the medical device.

Referring back to FIG. 3A, when the medical device 300 is in the open configuration, the medical device 300 can be moved around the urethra 30 through the gap 330 so that a urethra (not shown) is disposed within region L defined by the clamp component 310. After the clamp component 310 of the medical device 300 is moved around the urethra through the gap 330, the clamp component 310 of medical device 300 can be changed to the closed configuration shown in FIG. 3B so that the medical device 300 is clamped around the urethra. The crimp component 320 is configured to constrict (e.g., kink, lift, at least partially close off) a urethra when the medical device 300 is in the closed configuration around the urethra.

In some implementations, the end portions 312, 314 of the clamp component 310 can be configured so that the end portion 312 can be lockably coupled to the end portion 314 in a variety of positions when the clamp component 310 is in the closed configuration. In other words, the end portions 312, 314 can be adjustably coupled to one another. For example, the end portion 312 can be lockably coupled in a first position with respect to the end portion 314 (using at least a portion of the teeth) so that the clamp component 310 defines a circular shape, or substantially circular shape, having a first diameter. The end portion 312 can be moved with respect to the end portion 314 and lockably coupled in a second position with respect to the end portion 314 (using at least a portion of the teeth) so that the clamp component 310 defines a circular shape having a second diameter different from the first diameter. In some implementations, the end portions 312, 314 can be removably coupled so that the end portions 312, 314 can be moved from one lockably coupled configuration to another lockably coupled configuration.

In this implementation, the crimp component 320 is a strip of material, such as a mesh material, that can be adjusted using at least one of the arms 323, 324 of the crimp component 320 and a tension mechanism 322. In some implementations, the crimp component 320 can be referred to as an adjustable strap or as an adjustable mesh. In some implementations, the arms 323, 324 can be referred to as adjustable arms. One or more of the arms 323, 324 can be pulled so that tension of a portion 321 of the crimp component 320 disposed within the region L can be adjusted. In some implementations, one or more of the arms 323, 324 can be adjusted so that the tension of the crimp component 320, when constricting a urethra, can be adjusted. One or more of the arms 323, 324 can be slidably coupled to the clamp component 310. In some implementations, one or more of the arms 323, 324 can be coupled to the clamp component 310 via one or more openings therethrough at, for example, locations 317, 318. The arrangement of the crimp component 320 in this embodiment enables intraoperative and/or postsurgical adjustments (e.g., fine tuning adjustments). The intraoperative adjustments can be performed during an intraoperative time period and/or the postsurgical adjustments can be performed during a postsurgical time period. For example, after the medical device 300 has been placed around a lumen in a body of a patient and the end portion 312 is lockably coupled to the end portion 314, the crimp component 320 can be adjusted in a desirable fashion around the lumen.

As shown in FIGS. 3A and 3B, the portion 321 of the crimp component 320 can be moved along direction M when one or more of the arms 323, 324 are moved (e.g., pulled) along direction N, which in this implementation, is opposite (or substantially opposite) direction M. In some implementations, the tension mechanism 322 can be configured to fix the tension of the portion 321 of the crimp component 320. The portion 321 of the crimp component 320 can be configured to constrict a lumen of a patient so that a fluid is prevented, or substantially prevented, from flowing within the lumen. For example, a urethra of a patient can be constricted by the portion 321 of the crimp component 320 of the medical device 300 so that undesirable leakage associated with urinary incontinence can be prevented or substantially prevented. The portion 321 of the crimp component 320 of the medical device 300 can be configured so that voiding can be achieved when a patient bears down.

For example, the medical device 300 can be placed around a urethra of a patient, when in the open configuration shown in FIG. 3A, so that the urethra is in contact with the crimp component 320. After the medical device 300 is placed around the urethra of the patient, the medical device 300 can be changed to the closed configuration shown in FIG. 3B. One or more of the arms 323, 324 of the crimp component 320 can be pulled along direction N so that the portion 321 of the crimp component 320 moves along direction M to constrict, or further constrict, the urethra of the patient in a desirable fashion. In some implementations, one or more of the arms 323, 324 of the crimp component 320 can be adjusted, or relaxed, so that the portion 321 of the crimp component 320 can be loosened when around the urethra of the patient in a desirable fashion. The tension mechanism 322 can be moved, for example, slidably moved along the arms 323, 324 so that the tension of (or pressured applied by) the portion 321 of the crimp component 320 is maintained with a desirable level of tension. The tension of the portion 321 of the crimp component 320 can be adjusted so that the when a patient bears down, the patient can void through the medical device 300. As described above, intraoperative adjustments and/or postsurgical adjustments can be made to the crimp component 320 such that use of the medical device 300 by a patient when bearing down can be performed in a desirable fashion.

In some implementations, the tension component 322 can be configured to maintain, or substantially maintain, tension of the crimp component 320 using a variety of mechanisms such as friction, pressure, and so forth. In some implementations, the tension component 322 can be lockably coupled to one or more arms 323, 324 of the crimp component 320. In some implementations, the tension component 322 can be, or can include, sliding components, a clamp, a crimping component, a latch, loop and hook, etc.

Figure 3C:
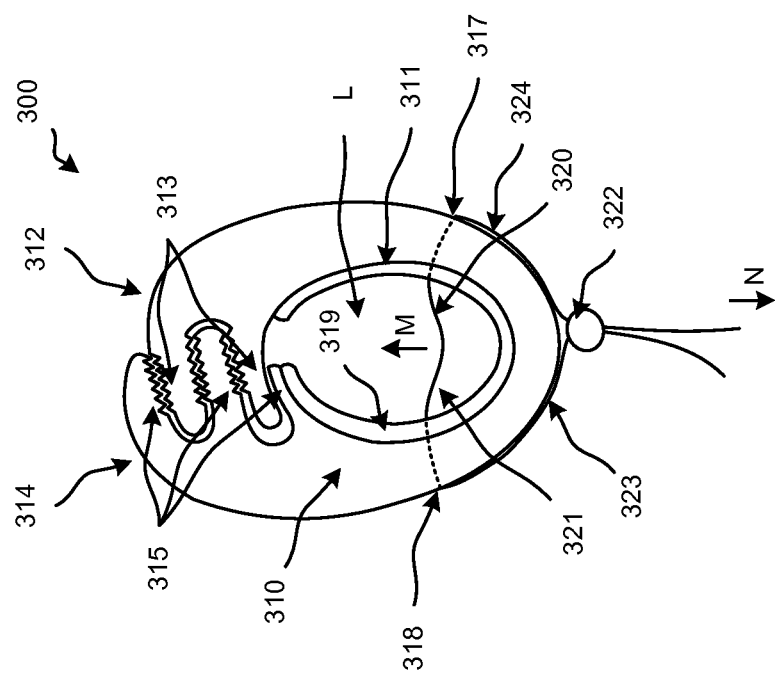

FIG. 3C is a diagram that illustrates the tension component 322 slidably moved to a position configured to maintain tension of the crimp component 320. As shown in FIG. 3C, the tension component 322 can be nearly in contact with or in contact with an outer surface of the clamp component 310. In some implementations, the portion 321 of the crimp component 320 can be taught when the tension component 322 is moved to the position shown in FIG. 3C. In some implementations, the portion 321 of the crimp component 320 can be applying pressure (or a kink) to a lumen such as a urethra taught when the tension component 322 is moved to the position shown in FIG. 3C.

When voiding by bearing down, a patient can cause at least a portion of the crimp component 320 (e.g., portion 321 of the crimp component 320) to move or flex. The tension component 322 can be configured to prevent, or substantially prevent, the tension of the crimp component 320 from changing after voiding has occurred many times. In other words, the tension component 322 can be configured to maintain, or substantially maintain, the tension of the crimp component 320 even after voiding has occurred many times.

Referring back to FIG. 3B, in some implementations, the crimp component 320 may have a single adjustable arm or tab. In such implementations, a portion of the crimp component 320 can be fixedly coupled to at least a portion of the clamp component 310. In some implementations, the crimp component 320 can have multiple different portions that can be used to adjust the tension of the crimp component 320. For example, a thread or filament can be threaded through at least a portion of the crimp component 320 so that when a force is applied to the thread or filament, the tension of the crimp component can be adjusted (e.g., constricted, loosened).

In some implementations, at least a portion of the crimp component 320 is made of a synthetic material such as a polymeric mesh body, a polymeric planar body without mesh cells and structures, and/or so forth. In some implementations, the synthetic material can include polypropylene, polyester, polyethylene, nylon, PVC, polystyrene, and/or so forth. In some implementations, a mesh body of the synthetic material can be made of a non-woven polymeric material. In some implementations, the synthetic material can include a Polyform® Synthetic Mesh developed by the Boston Scientific Corporation. The Polyform® Synthetic Mesh can be made from uncoated monofilament macroporous polypropylene. If made of a synthetic material such as a mesh, the mesh can have a specified weight. In some implementations, the mesh weight can be approximately between 15 g/cm$^2$ to 35 g/cm$^2$ (e.g., 20 g/cm$^2$, 25 g/cm$^2$, 30 g/cm$^2$). In some implementations, the crimp component 320 can be made of a synthetic material because the synthetic material can have a relatively high strength that can support a bodily portion such as a urethra without deforming (e.g., sagging, stretching) over time in an undesirable fashion compared with other materials.

In some implementations, at least a portion of the crimp component 320 shown in FIGS. 3A and 3B can be made of a biologic material such as an Allograft and/or a Xenograft. In some implementations, the biologic material can include cadaveric tissue, bovine dermis, porcine dermis, porcine intestinal sub mucosa, bovine pericardium, a cellulose based product, cadaveric dermis, and/or so forth. In some implementations, the Allograft materials can include Tutoplast®, Repliform®, DuraDerm®, Urogen®, and/or so forth. In some implementations, the Xenograft materials can include Xenoform® (e.g., Xenoform Matrix), Stratisis®, Dermatrix® and/or so forth. In some implementations, the crimp component 320 can be made of a biologic material because the biologic material can be relatively robust against tissue erosion.

As shown in FIGS. 3A and 3B, the clamp component 310 includes a liner 319. The liner 319 can be a relatively soft material (e.g., relatively low durometer) that is coupled to an inner surface 311 of the clamp component 310. The liner 319 can be configured to be in contact with, for example, a urethra of a patient when the clamp component 310 is disposed around the urethra. In some implementations, the liner 319 can be made of a material that is softer than a material that is used to produce the clamp component 310. Accordingly, in such implementations, the liner 319 can be configured to function as a relatively soft surface against which a tissue of a patient may come in contact instead of the harder material of the clamp component 310. In some implementations, the liner 319 can be made of a material that is softer than a material used to make the crimp component 321. In some implementations, the clamp component or liner may be fluid filled with, for example, saline or silicone. Additionally, in some implementations, the clamp component or liner may be filled with, covered with or include hydrogels, hyaluronic acid, etc. In some implementations, the clamp component 310 or liner 319 are sized and shaped to surround the urethra. In such implementations, the clamp component 310 or the liner 319 may be configured to apply pressure or compress the urethra at more than one location. For example, the liner may include a notch or a groove that is configured to receive a portion of the urethra or a portion of the circumference of the urethra. In some implementations, the clamp component 310 or liner 319 may have a long length or a short length. In some implementations, the length of the clamp component 310 or the length of the liner 319 will cause more or less compression or force to be applied to the urethra.

Although shown as being coupled to nearly all of the inner surface 311 of the clamp component 310, the liner 319 can be modified so that the liner is coupled to only a portion of the inner surface 311 of the clamp component 310. In some implementations, the liner 319 can be coupled to all of the inner surface 311 of the clamp component 310. In some implementations, the liner 319 can include multiple portions that are each separately coupled to portions of the inner surface 311 of the clamp component 310. In such implementations, portions of the liner 319 may or may not be in contact with one another.

In some implementations, the liner 319 can be made of any combination of a plastic material (e.g., a flexible plastic material), a silicone-based material, a rubber material (e.g., a rubber based material) and/or so forth. In some implementations, the liner 319 can be made of a single material or multiple materials. In some implementations, the liner 319 can be made of a material that substantially prevents or does not cause tissue erosion.

As shown in FIG. 3A, the liner 319 has a thickness P (along a side of the liner 319) that is thinner than a thickness R of the clamp component 310. The thickness R is shown along a side of the clamp component 310. In some implementations, the thickness of the side of the liner 319 can vary along different portions of the inner surface 311 of the clamp component 310. In some implementations, the thickness P of the liner 319 can be thinner than any portion of the side of the clamp component 310 (excluding the protrusions 313, 315 of the end portions 312, 314). In some implementations, the liner 319 can have a side thickness that is thicker than a side thickness of at least a portion of the clamp component 310.

In some implementations, the thickness R can be a few millimeters. In some implementations, the thickness R can be less than a few millimeters or greater than a few millimeters. In some implementations, the thickness P can be a millimeter or less. In some implementations, the thickness P can be greater than a millimeter.

In some implementations, the crimp component 320 can be made of a relatively flexible material compared with a material of the liner 319 and/or the clamp component 310 so that voiding can be achieved through a urethra when a patient bears down. Specifically, pressure applied by a fluid within the urethra can cause the crimp component 320 to flex at least along a direction opposite direction M so that the urethra may become less constricted (or have a larger opening) and permit flow of a fluid through the urethra. In some implementations, the crimp component 320 can be made of a material that substantially prevents or does not cause tissue erosion. In some implementations, the crimp component 320 may include soft materials, such as velvet, woven materials, non-woven materials, sponge materials, etc.

FIGS. 5A and 5B are diagrams that illustrate a medical device 500 configured to be implanted within a body of a patient. The medical device 500, which is an implementation of the medical device 100 shown in FIG. 1, is a bodily implant configured to be coupled to a urethra (not shown) for the treatment of urinary incontinence. The medical device 500 can be used, during a medical procedure, to treat various dysfunctions, including procedures to treat urinary incontinence. FIG. 5A illustrates the medical device 500 in an open configuration, and FIG. 5B illustrates the medical device 500 in a closed configuration.

As shown in FIG. 5A, the medical device 500 includes a clamp component 510 and a crimp component 520. When the medical device 500 is in the open configuration shown in FIG. 5A, an end portion 512 is separated from (e.g., is not lockably coupled to) an end portion 514 of the clamp component 510. The clamp component 510 is configured to be moved around a urethra (not shown) of a patient within region Q when the clamp component 510 is in the open configuration. The end portion 512 includes protrusions 513 that can be lockably coupled to protrusions 515 of the end portion 514 to form a closed configuration shown in FIG. 5B. The end portion 512 can be configured to be adjustably coupled to the end portion 514.

As with the other medical devices described herein, the medical device 500 shown in FIGS. 5A and 5B can be configured to constrict a lumen of a patient so that a fluid is prevented, or substantially prevented, from flowing within the lumen. For example, a urethra of a patient can be constricted by the crimp component 520 of the medical device 500 so that undesirable leakage associated with urinary incontinence can be prevented or substantially prevented. The medical device 500 can be configured so that voiding can be achieved even with the medical device 500 being disposed around the urethra of the patient when a patient bears down. In some implementations, the medical device 500 can be configured so that voiding can be achieved even when a patient bears down and caused the crimp component 520 to flex or move.

In this implementation, the crimp component 520 can be a solid material, or semi-solid material, that has a surface 521 coupled to a portion (e.g., a surface 517) of a liner 519 of the clamp component 510. The liner 519 can be configured to be in contact with, for example, a urethra of a patient when the clamp component 510 is disposed around the urethra. The crimp component 520 can be configured to compress when a force or pressure is applied to the crimp component 520. In some implementations, the crimp component 520 is configured to have approximately, or substantially, the same volume when compressed as when the crimp component 520 is not compressed. In other words, the crimp component 520 can be configured to change shape, but substantially not volume, in response to a force being applied to the crimp component 520. In some implementations, the crimp component 520 is not inflatable. In some implementations, the crimp component 520 is made of a porous material, or a relatively porous material, so that the crimp component 520 may not be inflated.

In some implementations, the crimp component 520 can be made of a relatively flexible material so that voiding can be achieved through a urethra when a patient bears down. Specifically, pressure applied by a fluid within the urethra can cause the crimp component 520 to flex at least along direction S so that the urethra may become less constricted (or have a larger opening) and permit flow of a fluid through the urethra. In some implementations, the crimp component 320 can be made of a material configured to flex or move in response to dilation with a urethral sound (or other dilation or probe device) during a medical procedure used to insert the medical device 500 into a body of a patient. More details related to use of a urethral sound during a medical procedure are described, for example, in connection with FIG. 11.

In some implementations, the crimp component 520 can be made of any combination of a plastic material (e.g., a flexible plastic material), a silicone-based material, a polymeric material, a rubber material (e.g., a rubber based material) and/or so forth. In some implementations, the crimp component 520 can be made of a single material. In some implementations, the crimp component 520 is made of several different materials. In some implementations, the crimp component 520 is made using several layers of material that coupled together. In some implementations, the crimp component 520 is made of a synthetic material can include polypropylene, polyester, polyethylene, nylon, PVC, polystyrene, and/or so forth. The crimp component 520 can be a relatively soft material that is softer than a material used to make the liner 519 and/or a material used to make the clamp component 520. In some implementations, the crimp component 520 can be configured to function as a relatively soft surface against which a tissue of a patient may come in contact instead of the harder material of the clamp component 510 and/or the liner 319.

As shown in FIGS. 5A and 5B, the crimp component 520 has a half-moon or semi-circular shape (or outer profile). An upper surface 518 of the crimp component 520 is flat, or substantially flat, and extends from one side of the clamp component 510 (e.g., a first portion of the liner 319 of the clamp component 510) to another side of the clamp component 510 (e.g., a second portion of the liner 319 the clamp component 510). As shown in FIGS. 5A and 5B, the crimp component 520 has a bottom surface coupled to approximately half or less than half of an inner perimeter of the substantially circular opening of the clamp component 510. In some implementations, the crimp component 520 has a bottom surface coupled to more than half of the inner perimeter of the substantially circular opening of the clamp component 510. In some implementations, the crimp component 520 can have a different shape or outer profile than that shown in FIGS. 5A and 5B. For example, in some implementations, the crimp component 520 can have a curved upper surface 518. In some implementations, the crimp component 520 can have one or more openings therethrough. In some implementations, the crimp component 520 can have a triangular shape, a square shape, and/or so forth.

Figure 6:
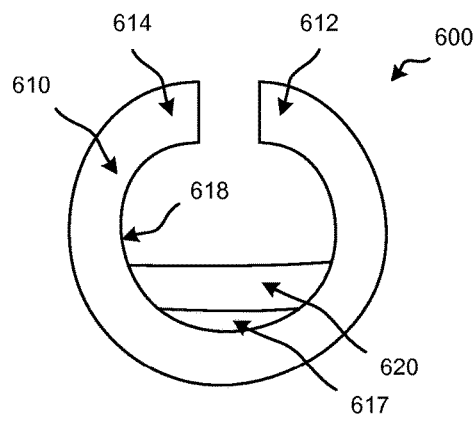
FIGS. 6 through 8 illustrate examples of crimp components.
Figure 7:
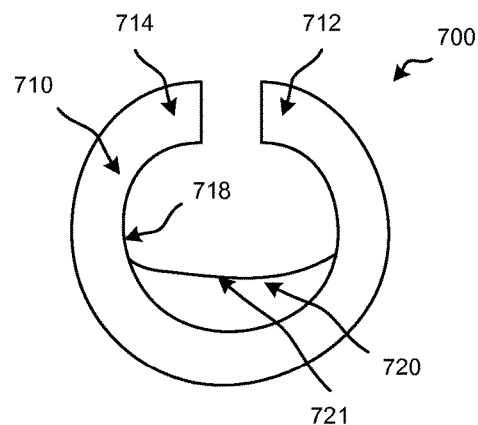
Figure 8:
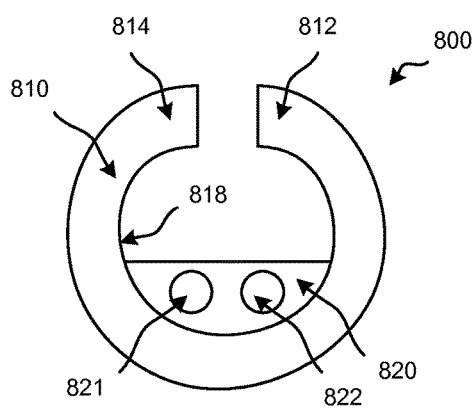

Example of different shapes of crimp components are shown in FIGS. 6 through 8. As shown in FIG. 6, a crimp component 620 is coupled to an inner surface 618 of a clamp component of a medical device 600, which includes end portions 612, 614. As shown in FIG. 6, an opening 617 is disposed between the crimp component 620 and the inner surface 618 of the clamp component 620.

As shown in FIG. 7, a crimp component 720 is coupled to an inner surface 718 of a clamp component of a medical device 700, which includes end portions 712, 714. The crimp component 720 is made of a monolithic piece of a material such as rubber, silicone, plastic and/or so forth. In this implementation, the crimp component 720 has a curved upper surface 721.

As shown in FIG. 8, a crimp component 820 is coupled to an inner surface 818 of a clamp component of a medical device 800, which includes end portions 812, 814. The crimp component 820 is made. In this implementation, the crimp component 820 has several features 821, 822 that can be recesses or holes therethrough. In some implementations, the crimp component 820 can include more than two features or less than two features such as those shown in FIG.

8. In some implementations, the features 821, 822 can have a different shape or outer profile than those shown in FIG. 8.

Figure 9:
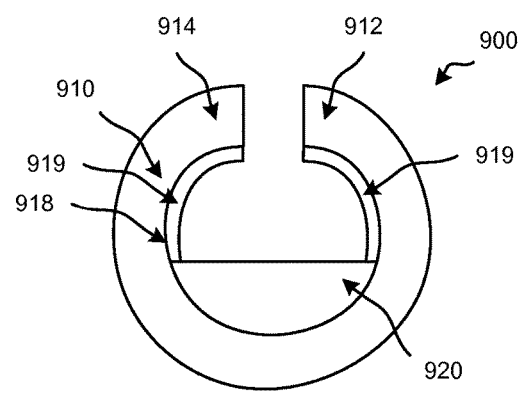
FIG. 9 illustrates a medical device with a liner that is coupled to a portion of an inner surface of a medical device.

In some implementations, one or more of FIGS. 6 through 8 can include a liner (not shown) such as liner 519 shown in FIGS. 5A and 5B. In some implementations, the liner can be coupled to only a portion of one or more of the crimp components 620, 720, 820. For example, FIG. 9 illustrates a medical device 900 with a liner 919 that is coupled to a portion of an inner surface 918 of the medical device 900 and abuts a crimp component 920. As shown in FIG. 9, the liner 919 includes two separate portions that may or may not be made of the same material.

Referring back to FIGS. 5A and 5B, in some implementations, the crimp component 520 can be replaced with another crimp component (not shown). In some implementations, the crimp component 520 can be removed and replaced with another crimp component before the medical device 500 is inserted into a body of the patient. In such implementations, the crimp component 520 can be replaced with another crimp component that can be a different shape (e.g., size, outer profile) than the crimp component 520 depending upon an anatomical feature of the patient. For example, if a lumen around which the medical device 500 is to be placed is relatively large, the crimp component 520 can be replaced with a smaller crimp component so that the region Q may be larger for the relatively large lumen. In some implementations, several crimp components can be included as part of a kit of the medical device 500.

Figure 10A:
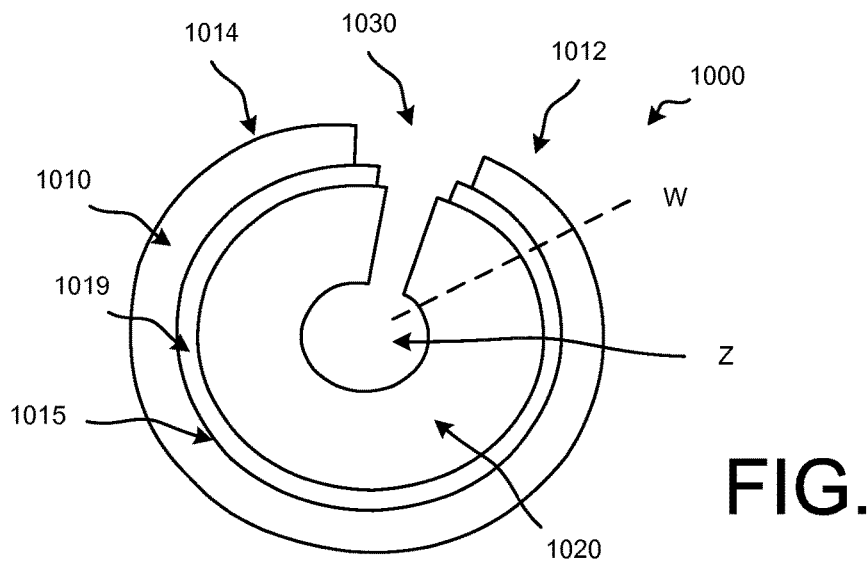
FIGS. 10A and 10B are diagrams that illustrate another medical device configured to be implanted within a body of a patient.
Figure 10B:
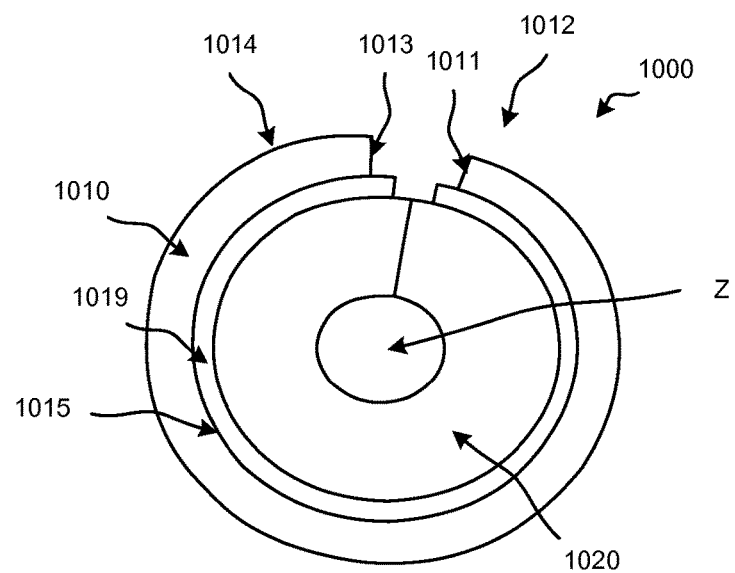

FIGS. 10A and 10B are diagrams that illustrate a medical device 1000 configured to be implanted within a body of a patient. The medical device 1000, which is an implementation of the medical device 100 shown in FIG. 1, is a bodily implant configured to be coupled to a urethra (not shown) for the treatment of urinary incontinence. The medical device 1000 can be used, during a medical procedure, to treat various dysfunctions, including procedures to treat urinary incontinence. FIG. 10A illustrates the medical device 1000 in an open configuration, and FIG. 10B illustrates the medical device 1000 in a closed configuration.

As shown in FIG. 10A, the medical device 1000 includes a clamp component 1010 and a crimp component 1020. When the medical device 1000 is in the open configuration shown in FIG. 10A, an end portion 1012 is separated from (e.g., is not lockably coupled to) an end portion 1014 of the clamp component 1010. The clamp component 1010 is configured to be moved around a urethra (not shown) of a patient within region Z when the clamp component 1010 is in the open configuration. The end portion 1012 can be configured to be lockably coupled to the end portion 1014 to form a closed configuration shown in FIG. 10B. The end portion 1012 can be configured to be adjustably coupled to the end portion 1014. In some implementations, the medical device 1000 can be biased to the closed configuration shown in FIG. 10B. In such implementations, the force can be applied to medical device 100 to move the medical device 100 to the open configuration shown in FIG. 10A.

As with the other medical devices described herein, the crimp component 1020 of the medical device 1000 shown in FIGS. 10A and 10B can be configured to constrict a lumen of a patient so that a fluid is prevented, or substantially prevented, from flowing within the lumen. In this implementation, the crimp component 1020 can be configured to surround (e.g., entirely surround, substantially surround) the lumen of the patient. In such implementations, the lumen of the patient can be circumferentially constricted rather than constricted on, for example, one side. For example, a urethra of a patient can be constricted by the crimp component 1020 of the medical device 1000 so that undesirable leakage associated with urinary incontinence can be prevented or substantially prevented. The medical device 1000 can be configured so that voiding can be achieved even with the medical device 1000 being disposed around the urethra of the patient when a patient bears down.

In this implementation, the crimp component 1020 can be a solid material, or semi-solid material, that has a surface 1021 coupled to a surface 1017 of the liner 1019 of the clamp component 1010. The crimp component 1020 can be configured to compress (e.g., compress radially outward from approximately the center of region Z) when a force or pressure is applied to the crimp component 1020 by a lumen disposed therein. In some implementations, the crimp component 1020 is configured to have approximately the same volume when compressed as when the crimp component 1020 is not compressed. In other words, the crimp component 1020 can be configured to change shape, but not volume, in response to a force being applied to the crimp component 1020. In some implementations, the crimp component 1020 is not inflatable. In some implementations, the crimp component 1020 is made of a porous material, or a relatively porous material, so that the crimp component 1020 may not be inflated.

Although not shown in FIGS. 10A and 10B, in some implementations, at least a portion of the crimp component 1020 can be directly coupled to surface 1015 of the clamp component 1010 (without at least a portion of the liner 1019). In some implementations, the medical device 1000 can be configured without the liner 1019, or with another liner in addition to liner 1019.

As shown in FIG. 10B, an end surface 1013 of the end portion 1014 is not in contact with an end surface 1011 of the end portion 1012 when the medical device 1000 is in the closed configuration. In some implementations, the end surface 1013 of the end portion 1014 can be in contact with the end surface 1011 of the end portion 1012 one medical device 1000 is in the closed configuration. Similarly, end surfaces of the liner 1019 are not in contact when the medical device 1000 is in the closed configuration. In some implementations, the end surfaces of the liner 1019 are in contact when the medical device 1000 is in the closed configuration. Also, in some configurations, end surfaces of the crimp component 1020 may not be in contact when the medical device 1000 is in the close configuration.

In some implementations, the crimp component 1020, the liner 1019, and the clamp component 1010 can have different levels of hardness. For example, the crimp component 1020 can be made of a harder or softer material than the liner 1019 and/or the clamp component 1010. In some implementations, the liner 1019 can be made of a material that is harder or softer than a material of the clamp component 1010.

Although the crimp component 1020 is illustrated as having a surface thickness (measured along line W) that is greater a surface thickness (measured along line W) that of the liner 1019 and/or a surface thickness (measured along line W) of the clamp component 1020, in some implementations, the crimp component 1020 can have a surface thickness that is less than that of the clamp component 1010 and/or the liner 1019. In some implementations, a surface thickness of the crimp component 1020, the liner 1019, and/or the clamp component 1020 can vary (e.g., taper, change) circumferentially. For example, a thickness of the clamp component 1010 at the end portion 1014 can be different than a thickness of the clamp component 1010 at the end portion 1012.

Figure 11:
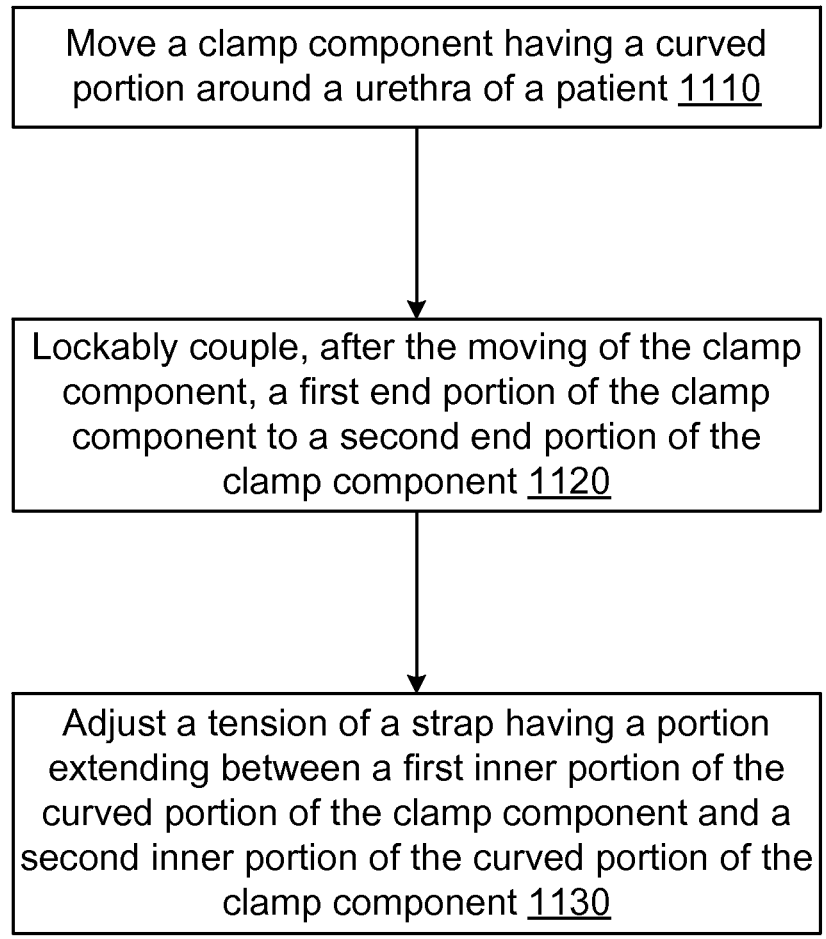
FIG. 11 is a flowchart that illustrates a method for inserting a medical device into a body of a patient.

FIG. 11 is a flowchart that illustrates a method for inserting a medical device into a body of a patient. The medical device can be any of the medical devices illustrated above such as medical device 100 shown in FIG. 1. In some implementations, the method can be performed during a medical procedure.

A clamp component having a curved portion is moved around a urethra of a patient (block 1110). In some implementations, the clamp component can be flexed so that the clamp component can be moved around the urethra of the patient. In some implementations, the clamp component can be moved around another lumen of the patient. In some implementations, the clamp component has a liner. In some implementations, the medical procedure can begin with perineal dissection of the bulb of the urethra. In some implementations, the medical device can be moved into the body of the patient through an incision in the body of the patient.

After the moving of the clamp component, a first end portion of the clamp component is lockably coupled to a second end portion of the clamp component (block 1120). In some implementations, the clamp component can be adjusted in a lockable configuration depending on the size of the urethra.

A tension of a strap having a portion extending between a first inner surface of the curved portion of the clamp component and a second inner surface of the curved portion of the clamp component is adjusted (block 1130). In some implementations, the tension can be adjusted using one or more arms of the strap outside of the clamp component. In some implementations, the tension can be adjusted using a tension mechanism and/or a crimp component. In some implementations, the strap can be referred to as an adjustable strap. As described above, intraoperative adjustments and/or postsurgical adjustments can be made using the adjustable strap.

In some implementations, when the tension of the strap is adjusted, at least a portion of the urethra can be lifted to cause a kink or constriction. In some implementations, a urethral sound inserted within the urethra can be used when adjusting the tension of the strap. The urethral sound can be used to prevent, or substantially prevent, the tension of the strap from being adjusted too loosely to prevent undesirable fluid flow through the urethra or adjusted too tightly so that fluid may be prevented from flowing through the urethra even when a patient bears down. In some implementations, the urethral sound (or other dilation or probe device) can be configured with a pressure transducer to assist in sizing or adjustment. In other words, the urethral sound, or other type of adjustment tool, can be configured with a pressure transducer so that the tension of the strap can be adjusted with a specified pressure or range of pressures.

In implementations where a crimp component is a solid or semi-solid material, a urethral sound inserted within the urethra can be used when adjusting the locking mechanism of the clamp component. In such implementations, the urethral sound can be used to prevent, or substantially prevent, the clamp component and crimp component from being adjusted too loosely to prevent undesirable fluid flow through the urethra or adjusted too tightly. As discussed above, the urethral sound can be configured with a pressure transducer so that the locking mechanism of the clamp component can be adjusted so that pressure from a crimp component can be applied with a specified pressure or range of pressures.

In some implementations, a medical device includes a clamp component and a strap. The clamp component has a portion configured to be placed around a urethra of a patient. The clamp component includes a first end portion configured to be lockably coupled to a second end portion of the clamp component. The strap has a portion extending between a first portion of the portion of the clamp component and a second portion of the portion of the clamp component.

In some implementations, the portion of the clamp component is curved or includes a curved portion. In some implementations, the portion of the strap is suspended between the first portion of the portion of the clamp component and the second portion of the portion of the clamp component. In some implementations, the first end portion includes a protrusion configured to be lockably coupled between two protrusions of the second end portion. In some implementations, the clamp component includes a liner coupled to an inner surface of the portion of the clamp component. In some implementations, the clamp component has an opening therethrough and the strap is configured to slidably move through the opening. In some implementations, the clamp component is made of a plastic material and the clamp component includes a liner coupled to an inner surface of the portion of the clamp component and made of material softer than the plastic material.

In some implementations, the strap includes an arm and the medical device includes a tension mechanism coupled to the arm of the strap. In some implementations, the strap includes at least one of a biologic material or a synthetic material.

In some implementations, a medical device includes a clamp component and a crimp component. The clamp component has a portion configured to be placed around a urethra of a patient. The clamp component including a first end portion configured to be lockably coupled to a second end portion of the clamp component. The clamp component includes a liner coupled to an inner surface of the portion of the clamp component. The crimp component has a surface extending between a first portion of the portion of the clamp component and a second portion of the portion of the clamp component. The crimp component is a non-inflatable component. In some implementations, the portion of the clamp component is curved or includes a curved portion.

In some implementations, the surface of the crimp component is a top surface, the clamp component defines a substantially circular opening when the first end portion of the clamp component is lockably coupled to the second end portion of the clamp component, and the crimp component has a bottom surface coupled to less than half of an inner perimeter of the substantially circular opening. In some implementations, the liner is made of a material harder than a material of the crimp component. In some implementations, the first portion of the portion of the clamp component is a first portion of the liner included in the clamp component, and the second portion of the portion of the clamp component is a second portion of the liner included in the clamp component. In some implementations, the first end portion includes locking teeth configured to be lockably coupled to locking teeth of the second end portion. In some implementations, the crimp component is made of a substantially solid material. In some implementations, the crimp component is made of at least one of a rubber material or a silicon material.

In some implementations, a method includes moving a clamp component having a portion around a urethra of a patient; lockably coupling, after the moving of the clamp component, a first end portion of the clamp component to a second end portion of the clamp component; and adjusting a tension of a strap having a portion extending between a first inner portion of the portion of the clamp component and a second inner portion of the portion of the clamp component.

In some implementations, the first inner portion is a first inner surface of a liner, and a second inner surface of the liner, and the method includes moving a position of a tension component along an arm of the strap such that the tension of the strap is substantially fixed during at least one of an intraoperative time period or a postsurgical time period.

In some implementations, the clamp component defines a substantially circular opening when the first end portion of the clamp component is lockably coupled to the second end portion of the clamp component, the portion of the strap is disposed within the opening, and the adjusting includes adjusting using an arm of the strap disposed outside of the opening.

In some implementations, the lockably coupling includes lockably coupling so that the clamp component surrounds the urethra of the patient, and the adjusting includes adjusting such that strap applies a force to the urethra of the patient. In some implementations, the method includes inserting a urethral sound into the urethra of the patient, and the adjusting the tension is based on pressure applied to the urethral sound.

Detailed implementations are disclosed herein; however, it is to be understood that the disclosed implementations are merely exemplary implementations, which may be implemented in various forms. Therefore, specific structural and functional details disclosed herein are to be interpreted as non-limiting, and as a basis for the claims and as a representative. In other words, while the disclosure includes preferred implementations shown and described in detail, various modifications and improvements thereon will become readily apparent to those skilled in the art. Any portion of the apparatus and/or methods described herein may be combined in any combination, except mutually exclusive combinations. The implementations described herein can include various combinations and/or sub-combinations of the functions, components and/or features of the different implementations described. Further, the terms and phrases used herein are not intended to be limiting, but to provide an understandable description of the invention. Accordingly, the spirit and scope of the present implementations are not to be limited by the foregoing examples, but it is to be understood in the broadest sense permitted.

What is claimed is:

1. A medical device, comprising:
a clamp component having a curved portion configured to be placed around a urethra of a patient, the clamp component including a first end portion configured to be lockably coupled to a second end portion of the clamp component, the first end portion including at least two protrusions configured to be lockably coupled between at least three protrusions of the second end portion via teeth disposed on the at least two protrusions of the first end portion, the clamp component defining an opening therethrough; and
an adjustable strap having a first portion extending between a first portion of the curved portion of the clamp component and a second portion of the curved portion of the clamp component, the first portion of the adjustable strap being disposed within the opening, the adjustable strap having a second portion disposed outside the opening defined by the clamp component,
wherein the second portion of the adjustable strap is configured to be pulled in a first direction such that the first portion of the adjustable strap moves in a second direction to constrict the urethra, and the second portion of the adjustable strap is configured to move in the second direction such that the first portion of the adjustable strap moves in the first direction to unconstrict the urethra, the first direction being opposite the second direction.

2. The medical device of claim 1, wherein the first portion of the adjustable strap is suspended between the first portion of the curved portion of the clamp component and the second portion of the curved portion of the clamp component.

3. The medical device of claim 1, wherein the clamp component includes a liner coupled to an inner surface of the curved portion of the clamp component.

4. The medical device of claim 1, wherein the clamp component is made of a plastic material, the clamp component including a liner coupled to an inner surface of the curved portion of the clamp component and made of material softer than the plastic material.

5. The medical device of claim 1, further comprising:
an adjustment locking mechanism coupled to the second portion of the adjustment strap.

6. The medical device of claim 1, wherein the adjustable strap includes at least one of a biologic material or a synthetic material.

7. A method, comprising:
moving a clamp component having a curved portion around a urethra of a patient;
lockably coupling, after the moving of the clamp component, a first end portion of the clamp component to a second end portion of the clamp component, the first end portion including at least two protrusions lockably coupled between at least three protrusions of the second end portion via teeth disposed on the at least two protrusions of the first end portion, the clamp component defining an opening therethrough; and
adjusting a tension of an adjustable strap, the adjustable strap having a first portion extending between a first portion of the curved portion of the clamp component and a second portion of the curved portion of the clamp component, the first portion of the adjustable strap being disposed within the opening, the adjustable strap having a second portion that is disposed outside of the opening of the clamp component,
wherein the adjusting the tension of the adjustable strap includes moving the second portion of the adjustable strap in a first direction such that the first portion of the adjustable strap moves in a second direction to constrict the urethra, and the second portion of the adjustable strap is configured to move in the second direction such that the first portion of the adjustable strap moves in the first direction to unconstrict the urethra, the first direction being opposite the second direction.

8. The method of claim 7, further comprising:
locking the second portion of the adjustable strap such that the tension of the adjustable strap is substantially fixed.

9. The method of claim 7, wherein the opening of the clamp component is a substantially circular opening when the first end portion of the clamp component is lockably coupled to the second end portion of the clamp component.

10. The method of claim 7, wherein the lockably coupling includes lockably coupling so that the clamp component surrounds the urethra of the patient, and the adjusting includes adjusting such that the adjustable strap applies a force to the urethra of the patient.

\* \* \* \* \*